(12) United States Patent
Poplett

(10) Patent No.: US 7,327,557 B2
(45) Date of Patent: Feb. 5, 2008

(54) METHOD AND APPARATUS FOR CONNECTING CAPACITOR ELECTRODES

(75) Inventor: James M. Poplett, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/379,693

(22) Filed: Apr. 21, 2006

(65) Prior Publication Data

US 2006/0256501 A1 Nov. 16, 2006

Related U.S. Application Data

(60) Provisional application No. 60/673,893, filed on Apr. 22, 2005.

(51) Int. Cl.
*H01G 4/228* (2006.01)
*H01G 9/10* (2006.01)
*H01G 9/00* (2006.01)

(52) U.S. Cl. .................. 361/520; 361/540; 361/533; 29/25.03

(58) Field of Classification Search ............... 361/516, 361/520, 540, 538, 532–533; 29/25.03
See application file for complete search history.

(56) References Cited

U.S. PATENT DOCUMENTS

| | | | |
|---|---|---|---|
| 2,021,455 A | 11/1935 | Lilienfeld | |
| 4,232,099 A | 11/1980 | Sullivan | |
| 4,614,194 A | 9/1986 | Jones et al. | |
| 4,659,636 A | 4/1987 | Suzuki et al. | |
| 4,907,130 A | 3/1990 | Boulloy et al. | |
| 5,801,917 A | 9/1998 | Elias | |
| 5,926,357 A | 7/1999 | Elias et al. | |
| 5,949,638 A | 9/1999 | Greenwood, Jr. et al. | |

(Continued)

FOREIGN PATENT DOCUMENTS

WO WO-0034964 A1 6/2000

(Continued)

OTHER PUBLICATIONS

"International Search Report and Written Opinion for Application No. PCT/US2006/015533, dated Aug. 17, 2006", 12 Pages.

(Continued)

*Primary Examiner*—Eric Thomas
(74) *Attorney, Agent, or Firm*—Schwegman, Lundberg & Woessner, P.A.

(57) ABSTRACT

A structure and method for connecting capacitor electrodes is provided. One aspect of this disclosure relates to an apparatus for connecting cathodes. The apparatus includes a cathode layer containing an aperture, and a connection member. The connection member includes a protrusion mateable to the aperture having a length at least equal to a thickness of the cathode layer, a first flat section perpendicular to the protrusion, the first flat section having a first side attached to the protrusion and a second side including a contact surface, and a second flat section perpendicular to the first flat section, the second flat section at an offset distance from the protrusion and having a height equal to or greater than the protrusion, and where the connection member is mated to the cathode layer. Other aspects and embodiments are provided herein.

20 Claims, 6 Drawing Sheets

U.S. PATENT DOCUMENTS

| | | | |
|---|---|---|---|
| 5,963,418 A * | 10/1999 | Greenwood et al. | 361/508 |
| 6,006,133 A | 12/1999 | Lessar et al. | |
| 6,110,233 A | 8/2000 | O'Phelan et al. | |
| 6,242,128 B1 | 6/2001 | Tura et al. | |
| 6,275,729 B1 | 8/2001 | O'Phelan et al. | |
| 6,413,283 B1 | 7/2002 | Day et al. | |
| 6,421,226 B1 | 7/2002 | O'Phelan et al. | |
| 6,509,588 B1 | 1/2003 | O'Phelan et al. | |
| 6,522,525 B1 | 2/2003 | O'Phelan et al. | |
| 6,556,863 B1 | 4/2003 | O'Phelan et al. | |
| 6,571,126 B1 | 5/2003 | O'Phelan et al. | |
| 6,621,686 B1 | 9/2003 | Jenn-Feng et al. | |
| 6,648,928 B2 | 11/2003 | Nielsen et al. | |
| 6,687,118 B1 | 2/2004 | O'Phelan et al. | |
| 6,699,265 B1 | 3/2004 | O'Phelan et al. | |
| 6,839,223 B2 * | 1/2005 | Kawahara et al. | 361/520 |
| 6,853,538 B2 | 2/2005 | O'Phelan et al. | |
| 6,861,670 B1 | 3/2005 | Ohtani et al. | |
| 6,885,548 B2 | 4/2005 | Nyberg | |
| 6,917,514 B2 * | 7/2005 | Mido et al. | 361/533 |
| 6,922,330 B2 | 7/2005 | Nielsen et al. | |
| 7,092,241 B2 | 8/2006 | Sherwood | |
| 2003/0056350 A1 | 3/2003 | Yan et al. | |
| 2003/0199940 A1 | 10/2003 | Nyberg | |
| 2003/0199942 A1 | 10/2003 | Nielsen et al. | |
| 2004/0085712 A1 | 5/2004 | Tadanobu et al. | |
| 2004/0147961 A1 | 7/2004 | O'Phelan et al. | |
| 2004/0220627 A1 | 11/2004 | Crespi et al. | |
| 2005/0017888 A1 | 1/2005 | Sherwood et al. | |
| 2006/0011963 A1 | 1/2006 | Poplett | |
| 2006/0012943 A1 | 1/2006 | Sherwood | |
| 2006/0166088 A1 | 7/2006 | Hokanson et al. | |

FOREIGN PATENT DOCUMENTS

WO    WO-2006116345 A1    11/2006

OTHER PUBLICATIONS

Sherwood, Gregory J., "Method and Apparatus for Providing Flexible Partially Etched Capacitor Electrode Interconnect", *U.S. Appl. No. 60/588,905, filed Jul. 16, 2004*, 241 Pages.

* cited by examiner

METHOD AND APPARATUS FOR CONNECTING CAPACITOR ELECTRODES

CROSS REFERENCE TO RELATED APPLICATIONS

This application claims the benefit of provisional U.S. patent application Ser. No. 60/673,893, filed on Apr. 22, 2005, which is hereby incorporated by reference in its entirety.

This application is related to the following commonly assigned U.S. patent applications which are herein incorporated by reference in their entirety: "Method and Apparatus for Single High Voltage Aluminum Capacitor Design," Ser. No. 60/588,905, filed on Jul. 16, 2004; "Method and Apparatus for Interconnecting Cathodes with Partial Titanium Coating," Ser. No. 11/124,706, filed on May 9, 2005; and "Method and Apparatus for Connecting Electrodes Having Apertures," Ser. No. 11/112,656, filed on Apr. 22, 2005.

TECHNICAL FIELD

This disclosure relates to electrolytic capacitors for implantable medical devices, particularly structures and methods for connecting electrodes in such capacitors.

BACKGROUND

Advances in the field of electronics manufacturing have decreased the achievable minimum feature size for electronic devices. Due to this reduction in device size, the required size of electrical interconnections for the devices is correspondingly reduced.

Electrolytic capacitors, such as those used within a defibrillator for delivering bursts of electric current to the human heart, are an example of an electronic device that has experienced a decrease in achievable feature size. To promote capacitor size reduction, new structures and methods for interconnecting electrodes within a capacitor are needed. Specifically, these new interconnections should provide efficient electrical charge transfer without causing damage to the capacitor or its subcomponents.

SUMMARY

The above-mentioned problems and others not expressly discussed herein are addressed by the present subject matter and will be understood by reading and studying this specification.

Disclosed herein, among other things, is an apparatus for connecting capacitor electrodes. The apparatus includes a cathode layer containing an aperture, and a connection member. The connection member includes a protrusion mateable to the aperture having a length at least equal to a thickness of the cathode layer, a first flat section perpendicular to the protrusion, the first flat section having a first side attached to the protrusion and a second side including a contact surface, and a second flat section perpendicular to the first flat section, the second flat section at an offset distance from the protrusion and having a height equal to or greater than the protrusion, and where the connection member is mated to the cathode layer.

One aspect of this disclosure relates to a method for interconnecting electrodes within an electrolytic capacitor. According to various embodiments, the method includes forming at least one cathode layer containing an aperture and forming a connection member, the connection member including: a protrusion mateable to the aperture and having a length at least equal to a thickness of the cathode layer; a first flat section perpendicular to the protrusion having a first side attached to the protrusion and a second side including a contact surface; and a second flat section perpendicular to the first flat section at an offset distance from the protrusion, having a height equal to or greater than the protrusion, and having an edge surface opposite the protrusion. The method further includes mating the connection member to the aperture and connecting the connection member of one cathode layer to a connection member of a second cathode layer.

One aspect of this disclosure relates to a capacitor stack. According to various embodiments, the capacitor stack includes at least one cathode layer containing an aperture and at least one connection member for each cathode layer, the connection member including: a protrusion mateable to the aperture having a length at least equal to a thickness of the cathode layer; a first flat section perpendicular to the protrusion having a first side attached to the protrusion and a second side including a contact surface; and a second flat section perpendicular to the first flat section at an offset distance from the protrusion, having a height equal to or greater than the protrusion, and having an edge surface opposite the protrusion. According to various embodiments, the connection member is mated to the cathode layer and the contact surface is suitable for contacting with an adjacent connection member to form a cathode interconnect.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. The various embodiments are not necessarily mutually exclusive, as aspects of one embodiment can be combined with aspects of another embodiment. These embodiments are described in sufficient detail to enable those skilled in the art to practice the invention. Other embodiments may be utilized and structural, logical, and electrical changes may be made without departing from the scope of the present invention.

Figure 1:
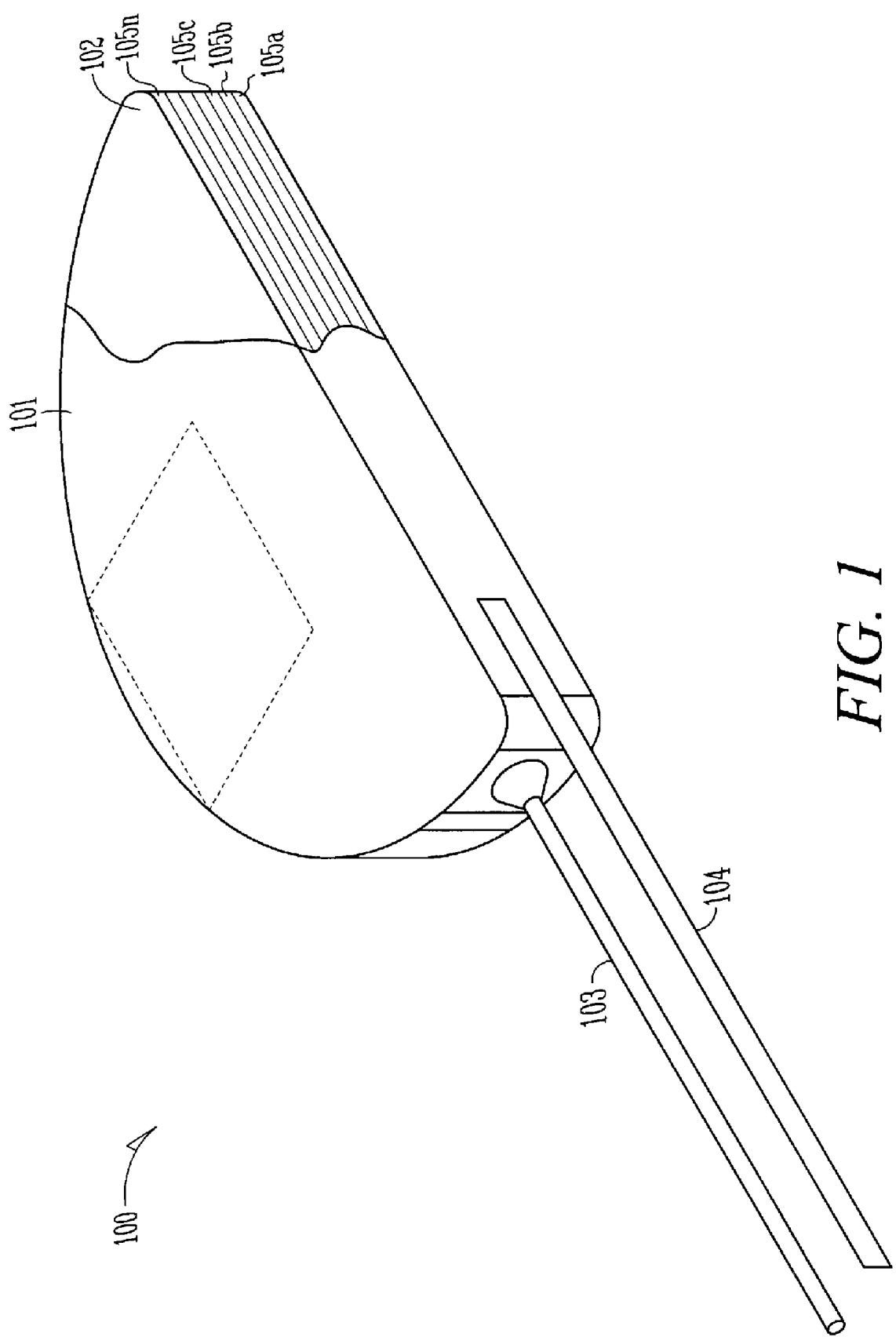
FIG. 1 illustrates an isometric view of a flat capacitor, according to various embodiments.

FIG. 1 illustrates an isometric view of a flat capacitor 100, according to various embodiments. Although capacitor 100 is a D-shaped capacitor, in other embodiments, the capacitor is another desirable shape, including, but not limited to rectangular, circular, oval or other symmetrical or asymmetrical shape. Capacitor 100 includes a case 101 which contains a capacitor stack 102. In the exemplary embodiment, case 101 is manufactured from a conductive material, such as aluminum. In other embodiments, the case is manufactured using a nonconductive material, such as a ceramic or a plastic.

Capacitor 100 includes a first terminal 103 and a second terminal 104 for connecting capacitor stack 102 to an outside electrical component, such as heart monitor circuitry, including defibrillator, cardioverter, and pacemaker circuitry. In the exemplary embodiment, terminal 103 is a feedthrough terminal insulated from case 101, while terminal 104 is directly connected to case 101. In other embodiments, the capacitor incorporates other connection methods, depending on other design factors. For instance, in some embodiments, capacitor 100 includes two or more feedthrough terminals 103.

Capacitor stack 102 includes capacitor elements 105a, 105b, 105c, . . . , 105n, with each capacitor element 105a-105n including one or more cathodes, anodes, and separators. Each cathode is a foil structure and can include aluminum, tantalum, hafnium, niobium, titanium, zirconium, and combinations of these metals. In one embodiment, each cathode of capacitor stack 102 is connected to the other cathodes by welding or other connection methods which will be discussed below. The cathodes are coupled to conductive case 101, and terminal 104 is attached to case 101 to provide a cathode connection to outside circuitry. In some embodiments, the cathode is coupled to a feedthrough conductor extending through a feedthrough hole.

The separator is located between each anode and cathode. In one embodiment, the separator includes one or more sheets of kraft paper impregnated with an electrolyte. In one embodiment, the separator includes two sheets of paper. The electrolyte can be any suitable electrolyte for an electrolytic capacitor, such as an ethylene-glycol base combined with polyphosphates, ammonium pentaborate, and/or an adipic acid solute.

In one embodiment, one or more of the anodes of capacitor stack 102 is a multi-anode stack which includes three foil layers. In other embodiments, one or more anode stacks include one, two, three or more anode foils having a variety of anode shapes. The anode foils are generally foil structures and can include aluminum, tantalum, hafnium, niobium, titanium, zirconium, and combinations of these metals. In one embodiment, at least portions of a major surface of each anode foil is roughened or etched to increase its effective surface area. This increases the capacitive effect of the foil with no relative increase in volume. Other embodiments incorporate other foil compositions and/or classes of foil compositions.

In one embodiment, each anode is connected to the other anodes of the capacitor and coupled to feedthrough assembly 103 for electrically connecting the anode to circuitry outside the case. In some embodiments, the anodes are connected to the case and the cathodes are coupled to a feedthrough assembly. In other embodiments, both the anode and the cathode are connected to feedthroughs.

Various embodiments include a capacitor stack adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

In various embodiments, the stack is disposed in a case, and linked with other components, a state which affects some of these values. For example, in one packaged embodiment, including a case and terminals, the energy density available ranges from about 5.3 joules per cubic centimeter of capacitor stack volume to about 6.3 joules per cubic centimeter of capacitor stack volume. Some embodiments are adapted to deliver about 5.8 joules. In various embodiments, these ranges are available at a voltage of between about 410 volts to about 610 volts.

Figure 2:
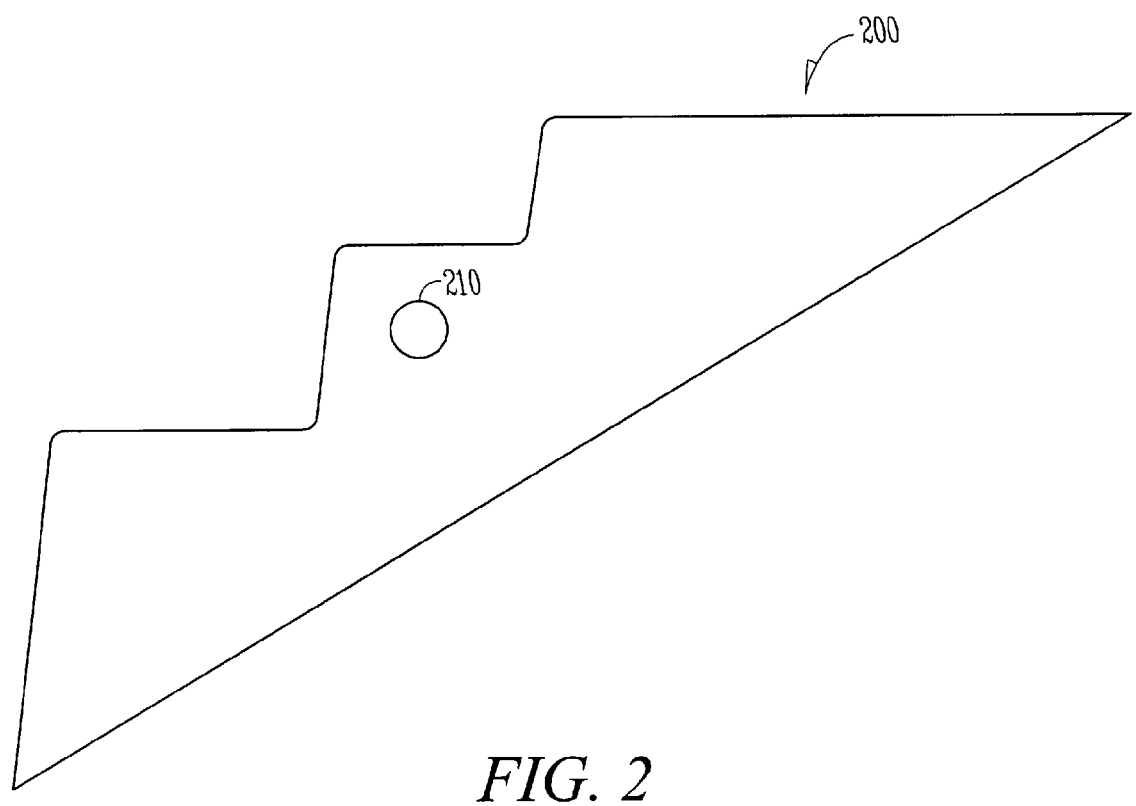
FIG. 2 illustrates a top view of a cathode layer with an aperture, according to various embodiments.

FIG. 2 illustrates a top view of a cathode layer 200 with an aperture 210, according to various embodiments. Cathode 200 is shown before it is assembled into capacitor stack 102 as shown in FIG. 1. In one embodiment, the aperture 210 includes a cylindrical pre-stamped hole in the cathode 200. In other embodiments, the aperture is a hole of various geometric shapes.

Figure 3:
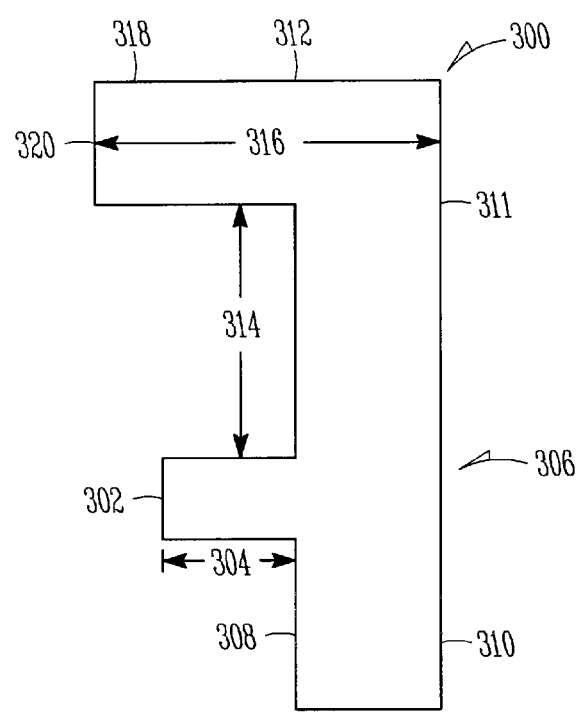
FIG. 3 illustrates a side view of a connection member, according to various embodiments.

FIG. 3 illustrates a side view of a connection member 300, according to various embodiments. The connection member 300 includes a protrusion 302 having a length 304 at least equal to a thickness of the cathode layer, and a first flat section 306 perpendicular to the protrusion 302, the first flat section 306 having a first side 308 attached to the protrusion and a second side 310 including a contact surface 311. The connection member 300 further includes a second flat section 312 perpendicular to the first flat section 306, the second flat section 312 at an offset distance 314 from the protrusion 302, having a height 316 equal to or greater than the protrusion 302, and having an edge surface 318 opposite the protrusion 302. The second flat section 312 further includes an end surface 320 perpendicular to the edge surface 318.

Figure 4A:
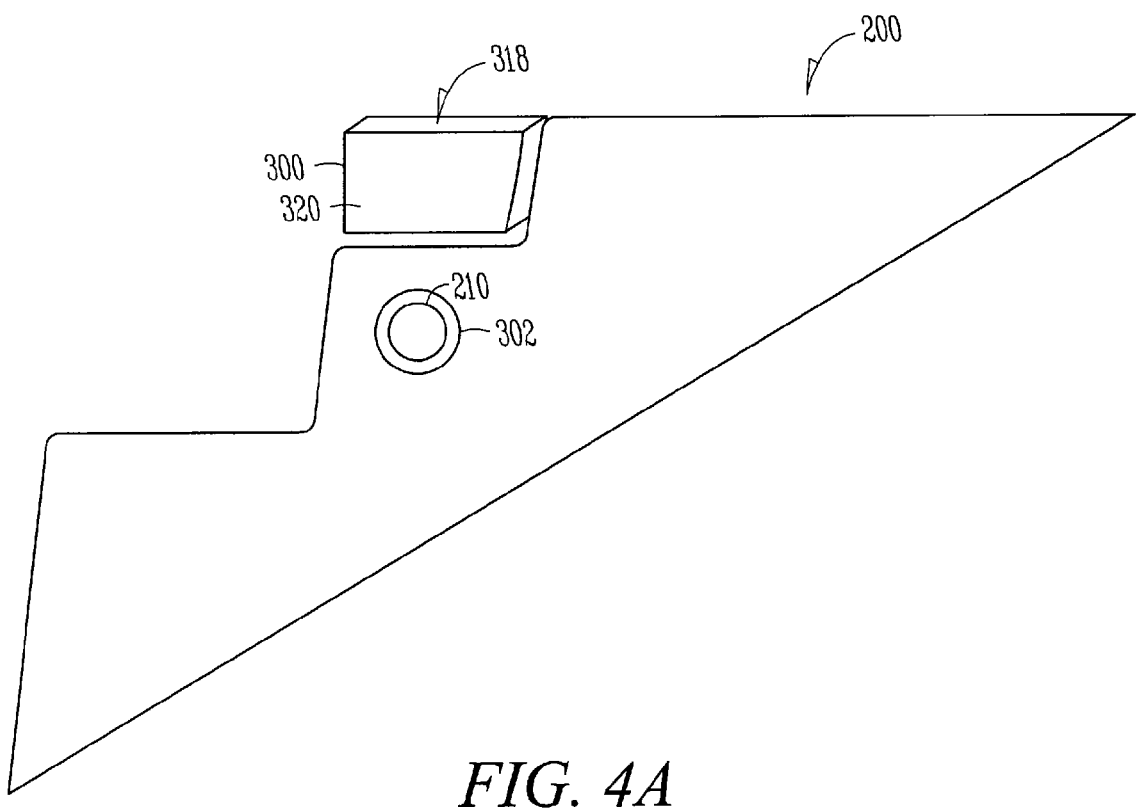
FIG. 4A illustrates a top view of a connection member mated to a cathode layer, according to various embodiments.

FIG. 4A illustrates a top view of a connection member 300 mated to a cathode layer 200, according to various embodiments. In one embodiment, the protrusion 302 includes a rivet. The rivet is placed through the aperture 210 and then compressed, forcing the connection member 300 into intimate contact with the cathode 200. The edge surface 318 and the end surface 320 of the connection member 300 are shown as positioned after mating the connection member and the cathode layer. In various embodiments, the connection member is welded, soldered or otherwise connected to the cathode layer after mating the protrusion to the aperture.

Figure 4B:
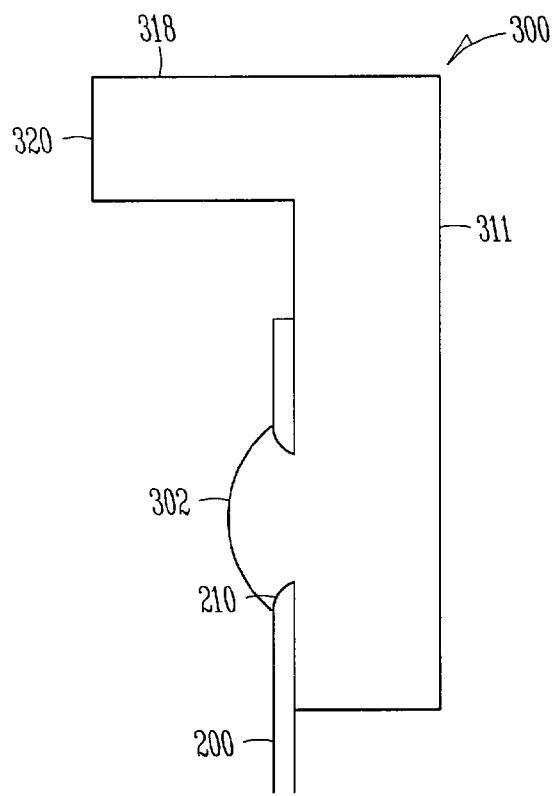
FIG. 4B illustrates a side view of a connection member mated to a cathode layer, according to various embodiments.

FIG. 4B illustrates a side view of a connection member 300 mated to a cathode layer 200, according to various embodiments. In the embodiment discussed above, the protrusion 302 includes a rivet. The rivet is placed through the aperture 210 and then compressed, forcing the connection member 300 into intimate contact with the cathode 200. The edge surface 318, the end surface 320 and the contact surface 311 are shown as positioned after mating the connection member and the cathode layer.

Other types of conductive interconnects may be used without departing from the present system. For example, the conductive interconnects may be made of a non-circular cross section. The conductive interconnects may be made of a suitable metal, such as aluminum. The conductive interconnects may also be made of other materials, including, but not limited to, conductive epoxy, conductive polymer (such as polyimide filled with aluminum), or fused aluminum powder. The metal used in the conductive interconnect should match the anode metal. Other anode metals/interconnect metal pairs may be used including, but not limited to, tantalum, hafnium, niobium, titanium, zirconium, or combinations of these metals.

Figure 5:
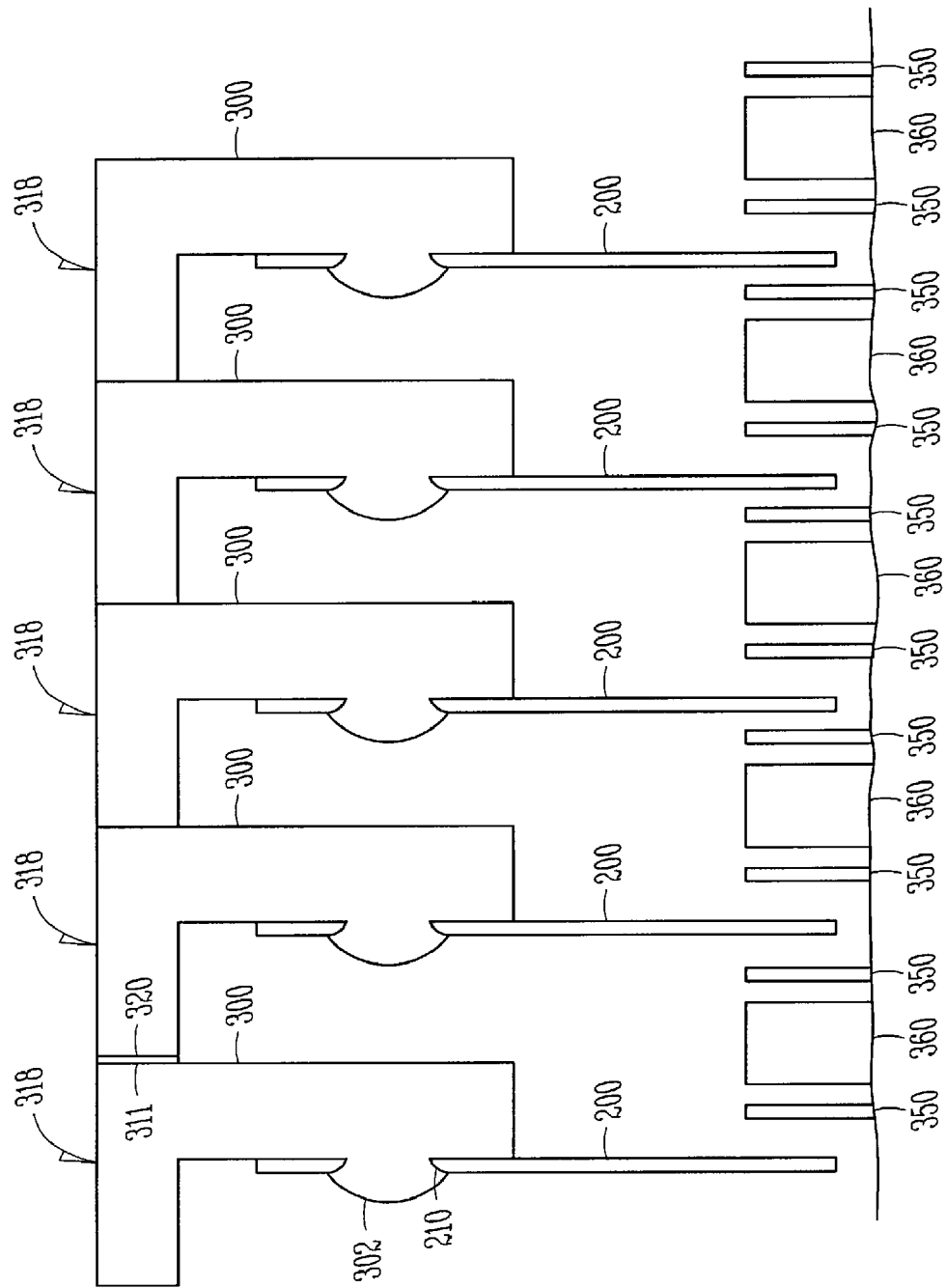
FIG. 5 illustrates a side view of a series of cathode layers with connection members, according to various embodiments.

FIG. 5 illustrates a side view of a series of cathode layers 200 with connection members 300, according to various embodiments. As disclosed above, each cathode layer 200 is mated to a connection member. An anode 360, or a layer of anodes, is placed between each cathode layer. A separator 350 is placed between each anode layer 360 and cathode 200. According to various embodiments, the connection member is sized to accommodate the width of the anodes and the separators between the cathodes. The contact surface 311 of one connection member abuts the end surface 320 of the adjoining connection member. The edge surface 318 of each connection member is aligned with the edge surface 318 of adjoining connection members. In one embodiment, the edge surfaces 318 are aligned to be substantially planar. The connection members 300 are then connected to form a cathode interconnect. In one embodiment, the connection members 300 are connected by welding along the edge surfaces 318, using a process called edge welding. Welding can be accomplished by laser, staking, aluminum sputter (spraying), ultrasonic welding, or other connection method.

The present disclosure has advantages over existing processes for creating cathode interconnects. Specifically, edge welding directly to a cathode layer as in prior art cleave-cut processes depends on the cathode layers, which are very thin, being connected in the edge weld. Even the slightest imperfection in alignment of the end of the cathode layers would cause the cathode connection area to be reduced. The present disclosure, utilizing designed connection members, allows for a more robust connection.

Figure 6:
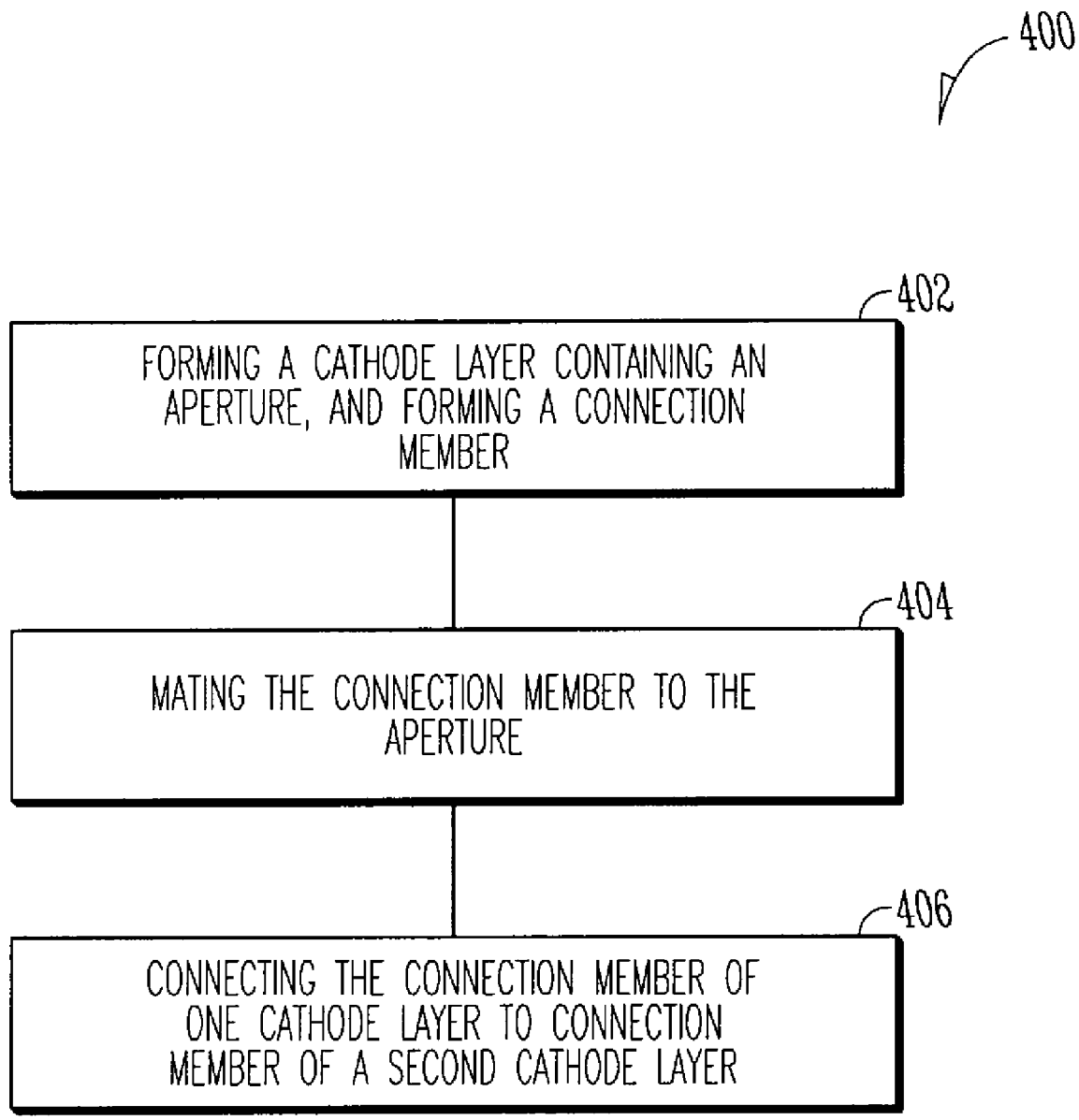
FIG. 6 illustrates a flow diagram of a method for connecting capacitor electrodes, according to various embodiments.

FIG. 6 illustrates a flow diagram of a method 400 for connecting capacitor electrodes, according to various embodiments. The method includes forming a cathode layer containing an aperture and forming a connection member, at 402. According to various embodiments, the connection member includes a protrusion mateable to the aperture, the protrusion having a length at least equal to a thickness of the cathode layer. According to various embodiments, the connection member further includes a first flat section perpendicular to the protrusion having a first side attached to the protrusion and a second side including a contact surface, and a second flat section perpendicular to the first flat section, the second flat section at an offset distance from the protrusion, having a height equal to or greater than the protrusion, and having an edge surface opposite the protrusion. The method further includes mating the connection member to the aperture, at 404, and connecting the connection member of one cathode layer to a connection member of a second cathode layer, at 406.

Various aspects of the present subject matter include performance properties which enable the capacitor to function as a single capacitor in an implantable cardioverter defibrillator. For example, by constructing the capacitor stack with the methods and apparatus contained in these teachings, one may construct a capacitor which is suited for use as the sole capacitor used for powering therapeutic pulses in an implantable cardioverter defibrillator.

One way to manufacture a capacitor according to the present teachings is to use a robotic assembly method, whereby anodes which are already masked, etched, and formed are stacked, followed by separator material, and then cathode material. In one assembly process, the cathodes are precision punched to provide accurately placed cathode holes. The robot can use the cathode features to accurately place the cathode relative to the anodes. A separator layer and an anode layer are also placed over the cathode using the robot. In embodiments where the conductive interconnect is a metal plug, the robot places the conductive plug accurately prior to the placement of the separator and anode layers. This process may be repeated to provide a stack of anodes of multiple layers interspersed with separator and cathode layers. The robot can also be used to perform the welding steps.

It is understood that other connections may be performed using the teachings provided herein. For example, it is possible to create a series of interconnections between anode layers using the teachings provided. Thus, use of the present system is not limited to cathode-cathode connections.

In one embodiment, the anode layers consist of a plurality of anode foils. In one application is it is possible that a single anode foil is interconnected to a triple anode foil or any multiplicity of anode foil combinations.

In one embodiment an anode layer may include a plurality of parts and/or layers. For example, the anode layer may include two different anode shapes in the same layer to provide a contoured edge. The shapes may be electrically connected to provide an equipotential surface. The use of multiple anode parts for a single layer facilitates the construction of a capacitor of virtually any form factor.

Furthermore, it is possible to weld multiple anode-cathode-anode stacks at different points for different conductive interconnects in one operation. Additionally, depending on the welding process used, several anode/cathode layers can be welded in a single operation.

Some of the benefits of the present system include, but are not limited to, the following: the electrical connection system provides mechanical stability; and alignment to the stack as the layers are being assembled; taping may not be required; the assembly is ready for insertion into the capacitor case; surface area is optimized; interior alignment is facilitated using interior features to align the stack layer to layer; and, in some embodiments, paper gluing may be eliminated.

Figure 7:
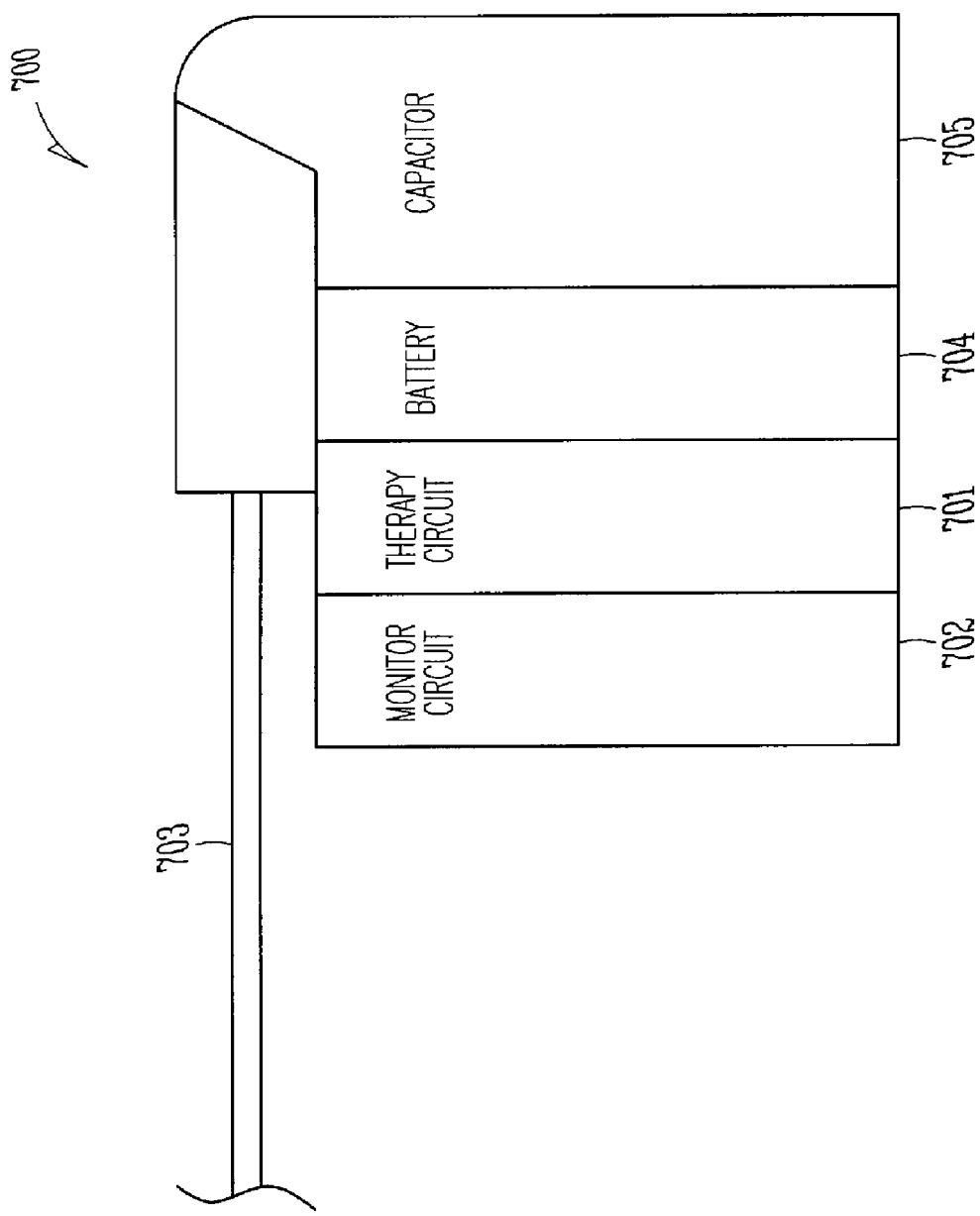
FIG. 7 illustrates a block diagram of a generic implantable medical device including a capacitor, according to various embodiments.

FIG. 7 illustrates a block diagram of a generic implantable medical device including a capacitor, according to various embodiments. An implantable heart monitor 700 is one of the many applications for capacitors incorporating one or more teachings of the present subject matter. As used herein, implantable heart monitor includes any implantable device for providing therapeutic stimulus to a heart muscle. Thus, for example, the term includes pacemakers, defibrillators, cardioverters, congestive heart failure devices, and combinations and permutations thereof.

Heart monitor 700 includes a lead system 703, which after implantation electrically contact strategic portions of a patient's heart. Shown schematically are portions of monitor 700 including a monitoring circuit 702 for monitoring heart activity through one or more of the leads of lead system 703, and a therapy circuit 701 for delivering electrical energy through one or more of the leads to a heart. Monitor 700 also includes an energy storage component, which includes a battery 704 and incorporates at least one capacitor 705 having one or more of the features of the exemplary capacitors described above.

In addition to implantable heart monitor and other cardiac rhythm management devices, one or more teachings of the present invention can be incorporated into cylindrical capacitors and/or capacitors used for photographic flash equipment. Indeed, teachings of the invention are pertinent to any application where high-energy, high-voltage, or space-efficient capacitors are desirable. Moreover, one or more teachings are applicable to batteries.

In furtherance of the art, the inventors have devised connection structures and methods for interconnecting the anode foils and the cathode foils of capacitors. Among other advantages, the exemplary method provides a more robust electrode connection when constructing a capacitor.

This disclosure includes several processes, circuit diagrams, and structures. The present invention is not limited to a particular process order or logical arrangement. Although specific embodiments have been illustrated and described herein, it will be appreciated by those of ordinary skill in the art that any arrangement which is calculated to achieve the same purpose may be substituted for the specific embodiment shown. This application is intended to cover adaptations or variations, and includes any other applications in which the above structures and fabrication methods are used. It is to be understood that the above description is intended to be illustrative, and not restrictive. Combinations of the above embodiments, and other embodiments, will be apparent to those of skill in the art upon reviewing the above description. The scope of the present invention should be determined with reference to the appended claims, along with the full scope of equivalents to which such claims are entitled.

What is claimed is:

1. An apparatus comprising:
   a cathode layer containing an aperture; and
   a connection member including:
      a protrusion mateable to the aperture, the protrusion having a length at least equal to a thickness of the cathode layer;
      a first flat section perpendicular to the protrusion, the first flat section having a first side attached to the protrusion and a second side including a contact surface; and
      a second flat section perpendicular to the first flat section, the second flat section at an offset distance from the protrusion and having a height equal to or greater than the protrusion; and
   wherein the connection member is mated to the cathode layer.

2. The apparatus of claim 1, wherein the protrusion includes a rivet.

3. The apparatus of claim 2, wherein the rivet is compressed to mate to the cathode layer.

4. The apparatus of claim 1, wherein the contact surface is suitable for contacting with an adjacent connection member to form a cathode interconnect.

5. A capacitor stack comprising:
   at least one cathode layer containing an aperture; and
   at least one connection member for each cathode layer, the connection member including:
      a protrusion mateable to the aperture, the protrusion having a length at least equal to a thickness of the cathode layer;
      a first flat section perpendicular to the protrusion, the first flat section having a first side attached to the protrusion and a second side including a contact surface; and
      a second flat section perpendicular to the first flat section, the second flat section at an offset distance from the protrusion, having a height equal to or greater than the protrusion, and having an edge surface opposite the protrusion;
   wherein the connection member is mated to the cathode layer; and
   wherein the contact surface is suitable for contacting with an adjacent connection member to form a cathode interconnect.

6. The capacitor stack of claim 5, further comprising:
   at least one anode layer parallel to the cathode layer; and
   a separator material separating the cathode layer from the anode layer.

7. The capacitor stack of claim 6, wherein the anode layer includes a thin aluminum foil.

8. The capacitor stack of claim 6, wherein the separator material includes kraft paper.

9. The capacitor stack of claim 6, wherein the second flat section of the connection member has a length sufficient to accommodate the width of the anode layer and the separator between cathode layers.

10. The capacitor stack of claim 5, wherein the cathode layer includes a thin aluminum foil.

11. The capacitor stack of claim 5, wherein the protrusion includes a rivet.

12. The capacitor stack of claim 11, wherein the rivet is compressed to mate to the cathode layer.

13. The capacitor stack of claim 5, wherein the cathode interconnect includes a weld across the edge surfaces of a plurality of connection members.

14. A method for connecting capacitor cathodes, comprising:
   forming at least one cathode layer containing an aperture;
   forming a connection member, the connection member including:
      a protrusion mateable to the aperture, the protrusion having a length at least equal to a thickness of the cathode layer;
      a first flat section perpendicular to the protrusion, the first flat section having a first side attached to the protrusion and a second side including a contact surface; and
      a second flat section perpendicular to the first flat section, the second flat section at an offset distance from the protrusion, having a height equal to or greater than the protrusion, and having an edge surface opposite the protrusion;
   mating the connection member to the aperture; and
   connecting the connection member of one cathode layer to a connection member of a second cathode layer.

15. The method of claim 14, further comprising:
   forming at least one anode layer parallel to the cathode layer; and
   separating the cathode layer from the anode layer using a separator material.

16. The method of claim 14, further comprising aligning the edge surfaces of adjoining cathode layers to be substantially planar before connecting the connection members.

17. The method of claim 14, wherein forming at least one cathode layer containing an aperture includes forming a cylindrical aperture in the cathode layer.

18. The method of claim 17, wherein the protrusion has a cylindrical shape.

19. The method of claim 14, wherein connecting the connection member of one cathode layer to the connection member of a second cathode layer includes placing the respective contact surfaces against one another and welding along the respective edge surfaces.

20. The method of claim 14, wherein mating the connection member to the aperture includes riveting the connection member to the aperture.

* * * * *

UNITED STATES PATENT AND TRADEMARK OFFICE
CERTIFICATE OF CORRECTION

PATENT NO. : 7,327,557 B2
APPLICATION NO. : 11/379693
DATED : February 5, 2008
INVENTOR(S) : Poplett It is certified that error appears in the above-identified patent and that said Letters Patent is hereby corrected as shown below:

In columns 4 and 5, lines 63-67 (Col. 4) and 1-8 (Col. 5), delete "Other types of conductive interconnects may be used without departing from the present system. For example, the conductive interconnects may be made of a non-circular cross section. The conductive interconnects may be made of a suitable metal, such as aluminum. The conductive inter- connects may also be made of other materials, including, but not limited to, conductive epoxy, conductive polymer (such as polyimide filled with aluminum), or fused aluminum powder. The metal used in the conductive interconnect should match the anode metal. Other anode metals/interconnect metal pairs may be used including, but not limited to, tantalum, hafnium, niobium, titanium, zirconium, or combinations of these metals." and insert the same on Col. 6, Line 10, below "steps." as a new paragraph.

Signed and Sealed this

Third Day of June, 2008

JON W. DUDAS
*Director of the United States Patent and Trademark Office*